US007495011B2

(12) United States Patent
Fujii et al.

(10) Patent No.: US 7,495,011 B2
(45) Date of Patent: Feb. 24, 2009

(54) ANTI-CORONAVIRUS DRUG

(75) Inventors: Nobutaka Fujii, Otsu (JP); Naoki Yamamoto, Tokyo (JP)

(73) Assignee: aRigen Pharmaceuticals, Inc., Tokyo (JP)

(*) Notice: Subject to any disclaimer, the term of this patent is extended or adjusted under 35 U.S.C. 154(b) by 298 days.

(21) Appl. No.: 10/564,557

(22) PCT Filed: Jul. 14, 2004

(86) PCT No.: PCT/JP2004/010352

§ 371 (c)(1),
(2), (4) Date: Mar. 28, 2006

(87) PCT Pub. No.: WO2005/004868

PCT Pub. Date: Jan. 20, 2005

(65) Prior Publication Data

US 2006/0223847 A1 Oct. 5, 2006

(30) Foreign Application Priority Data

Jul. 15, 2003 (JP) ............................ 2003-274886

(51) Int. Cl.
*C07D 217/02* (2006.01)
*A61K 31/47* (2006.01)

(52) U.S. Cl. ...................................... 514/310; 546/146

(58) Field of Classification Search ....................... None
See application file for complete search history.

(56) References Cited

U.S. PATENT DOCUMENTS

| | | | |
|---|---|---|---|
| 5,484,926 | A | 1/1996 | Dressman et al. |
| 5,824,688 | A | 10/1998 | Kalish et al. |
| 5,827,859 | A | 10/1998 | Kalish et al. |
| 5,827,891 | A | 10/1998 | Dressman et al. |

FOREIGN PATENT DOCUMENTS

| | | | |
|---|---|---|---|
| CN | 1131942 | A | 9/1996 |
| JP | 9-501443 | A | 2/1997 |
| JP | 9501443 | T | 2/1997 |
| WO | WO02/089835 | | 11/2002 |
| WO | WO2004/108151 | | 12/2004 |

OTHER PUBLICATIONS

Holmes, "SARS coronavirus: a new challenge for prevention and therapy," The Journal of Clinical Investigation, vol. 111, No. 11, pp. 1605-1609, Jun. 2003.

Cinatl, J. et al., "Glycyrrhizin, an active component of liquorice roots, and replication of SARS-associated coronavirus," The Lancet, vol. 361, pp. 2045-2046 (2003).

Yamaoto, N. et al., "HIV protease inhibitor nelfinavir inhibits replication of SARS-associated coronavirus," Biochemical and Biophysical Research Communications, vol. 318, pp. 719-725 (2004).

Patrick, A.K. et al., "Antiviral and resistance studies of AG1343, an orally bioavailable inhibitor of human immunodeficiency virus protease," Antimicrobial Agents and Chemotherapy, vol. 40, No. 2, pp. 292-297 (1996).

*Primary Examiner*—Zinna N Davis
(74) *Attorney, Agent, or Firm*—Fitch, Even, Tabin & Flannery

(57) ABSTRACT

The present invention provides an anti-coronavirus agent including as an active ingredient as exemplified by nelfinavir and salts thereof, an anti-SARS agent including the anti-coronavirus agent, and a method of treating SARS using the anti-SARS agent.

3 Claims, 1 Drawing Sheet

ANTI-CORONAVIRUS DRUG

This Application is the National Phase of International Application No. PCT/JP2004/010352 filed Jul. 14, 2004, which designated the U.S. and was not published under PCT Article 21(2) in English, and this application claims, via the aforesaid International Application, the foreign priority benefit of and claims the priority from Japanese Application No. 2003-274886, filed Jul. 15, 2003, the complete disclosures of which are incorporated herein by reference.

TECHNICAL FIELD

The present invention relates to an anti-coronavirus agent, an anti-SARS agent, and a method for treating SARS.

BACKGROUND ART

In 2003, there was an outbreak of SARS (Severe Acute Respiratory Syndrome) in Asian countries (*The Journal of the Japanese Association for Infectious Diseases*, Vol. 77, No. 5, pp. 303-309, ). However, the coronavirus which causes SARS is a previously unrecognized virus (SARS-associated coronavirus; hereinafter referred to as the “SARS virus”), and effective drugs for treating diseases caused by this virus have not yet been found.

Professor David D. Ho et al. of the Rockefeller University have reported their findings that T20 (Fuseon), a fusion inhibitor for HIV, is also effective against the SARS virus.

Nevertheless, various anti-HIV agents such as T20 have exhibited barely any efficacy against the SARS virus. Further, the finding that glycyrrhizin is effective against the SARS virus has been announced (*THE LANCET*, 361, pp. 2045-46, 2003), but it exhibits extremely limited potency.

DISCLOSURE OF THE INVENTION

The primary object of the present invention is to provide a compound or an agent with high anti-coronavirus activity.

The inventors of the present invention have uniquely analyzed using bioinformatics the genome of the SARS virus that the CDC has sequenced, and have found that the mechanism by which HIV (Human Immunodeficiency Virus) infects humans is similar to that the SARS virus uses to infect humans. Based on this finding, the inventors have conducted extensive research and found that specific compounds among known anti-HIV drugs have high anti-coronavirus activity, whereby the present invention has been accomplished. Stated more specifically, the present invention provides the following an anti-coronavirus agent, an anti-SARS agent, and a method for treating SARS.

Item 1 An anti-coronavirus agent comprising as an active ingredient a compound represented by formula (1):

Formula (1)

(1)

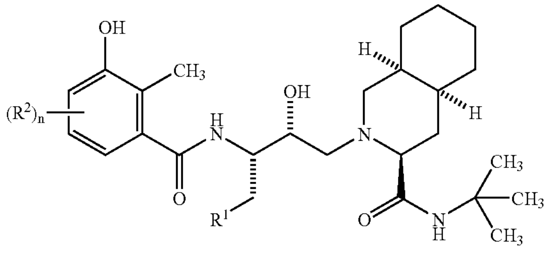

wherein $R^1$ represents formula (2) or (3) below:

Formula (2)

(2)

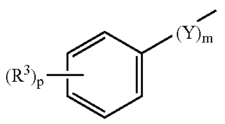

wherein Y is S, O or NH; each $R^3$ is independently a $C_1$-$C_4$ alkyl group, $C_1$-$C_4$ alkoxyl group, $C_1$-$C_4$ alkylamino group, amido group, carboxy group, amino group, hydroxy group, or halogen atom; m is 0 or 1, and p is an integer from 0 to 5

Formula (3)

(3)

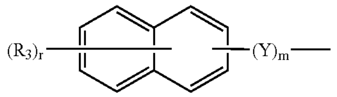

wherein Y, $R^3$ and m are as above; and r is an integer from 0 to 6;

each $R^2$ is independently a $C_1$-$C_4$ alkyl group, $C_1$-$C_4$ alkoxy group, $C_1$-$C_4$ alkylamino group, amido group, carboxy group, amino group, hydroxy group, halogen atom; and n is an integer from 0 to 3;

or a pharmaceutically acceptable salt thereof.

Item 2 An anti-coronavirus agent according to Item 1, wherein $R^1$ in formula (1) is formula (4)

Formula (4)

(4)

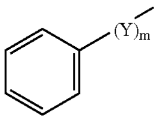

wherein Y represents S, O or NH; and m is 0 or 1.

Item 3 An anti-coronavirus agent according to Item 1, wherein the compound represented by formula (1) is the compound represented by formula (5).

Formula (5)

(5)

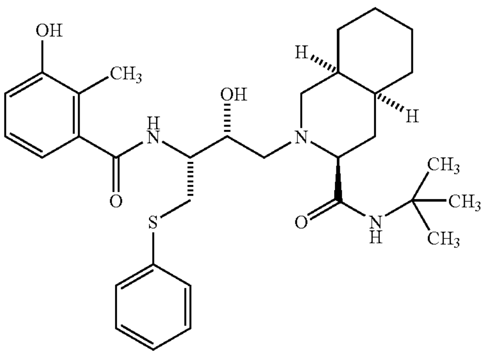

Item 4 An anti-coronavirus agent according to any one of Items 1 to 3, wherein the coronavirus is a SARS-associated coronavirus.

Item 5 An anti-coronavirus agent according to any one of Items 1 to 4, wherein the pharmaceutically acceptable salt of the compound represented by formula (1) is a methanesulfonate.

Item 6 An anti-SARS agent comprising the anti-coronavirus agent according to any one of Items 1 to 5 as an active ingredient, and a pharmaceutically acceptable carrier, excipient and/or diluent.

Item 7 A method for treating SARS using the anti-SARS agent according to Item 6.

MEANS FOR SOLVING PROBLEM

Figure 1:
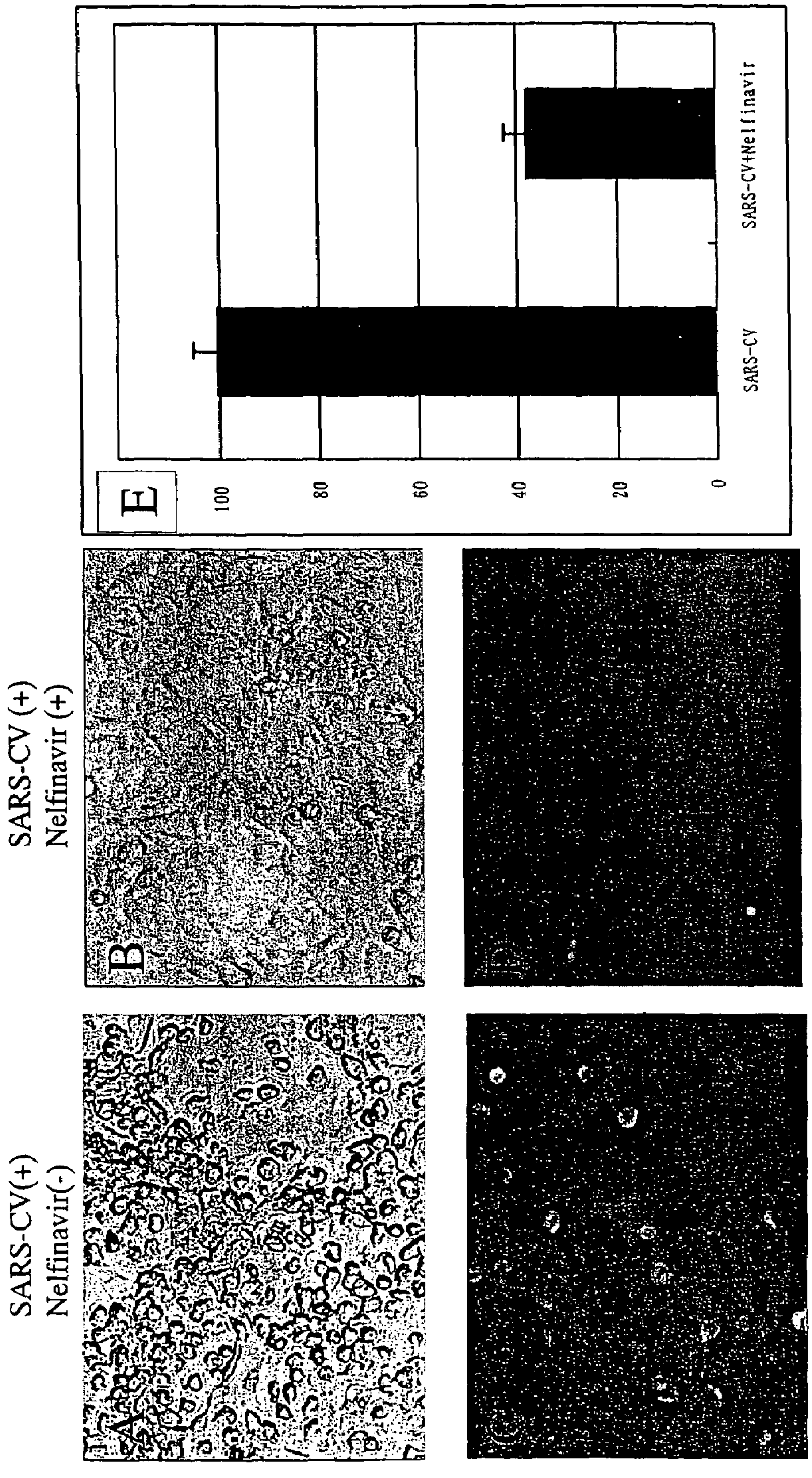
FIG. 1 respectively shows the result of SARS virus culturing in the presence or absence of nelfinavir. A is an electron micrograph of verotoxin in the absence of nelfinavir, B is an electron micrograph of verotoxin in the presence of nelfinavir, C is the result of immunofluorescence staining in the absence of nelfinavir, D is the result of immunofluorescense antibody staining in the presence of nelfinavir and E is RNA level (E) of the SARS virus in verotoxin.

The anti-coronavirus agent of the present invention comprises as an active ingredient a compound represented by formula (1):

(1)

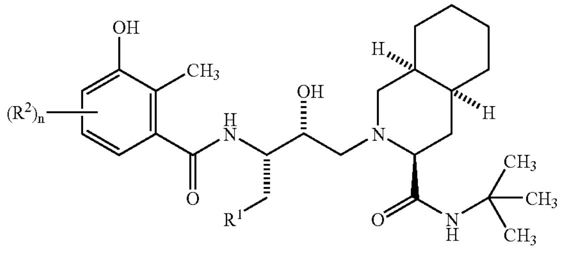

wherein $R^1$ represents formula (2) or (3) below: Formula (2)

(2)

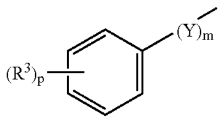

wherein Y is S, O or NH; each $R^3$ is independently a $C_1$-$C_4$ alkyl group, $C_1$-$C_4$ alkoxyl group, $C_1$-$C_4$ alkylamino group, amido group, carboxy group, amino group, hydroxy group, or halogen atom; m is 0 or 1, and p is an integer from 0 to 5 Formula (3)

(3)

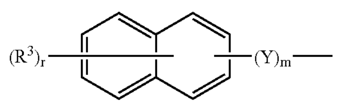

wherein Y, $R^3$ and m are as above; and r is an integer from 0 to 6;

each $R^2$ is independently a $C_1$-$C_4$ alkyl group, $C_1$-$C_4$ alkoxy group, $C_1$-$C_4$ alkylamino group, amido group, carboxy group, amino group, hydroxy group, or halogen atom; and n is an integer from 0 to 3;

or a pharmaceutically acceptable salt thereof.

The anti-SARS agent according to the present invention comprises the anti-coronavirus agent of the present invention as an active ingredient and a pharmaceutically acceptable carrier, excipient and/or diluent. Furthermore, the method of treating SARS according to the invention uses the anti-SARS agent of the invention.

In formula (1), a preferable example of $R^1$ is represented by formula (4) below:

Formula (4)

(4)

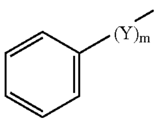

wherein Y is S, O or NH; and m is 0 or 1.

A more preferable example of $R^1$ is represented by the following formula (6):

(6)

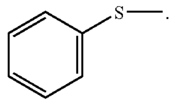

In each of the above formulas (1) to (5), when a plurality of $R^2$ are present, these substituents may all be the same or they may be different. When a plurality of $R^3$ and $R^4$ are both present, these substituents may all be the same or they may be different.

$C_1$-$C_4$ alkyl groups may be linear or branched. Preferable examples of such groups are methyl, ethyl, n-propyl, isopropyl, n-butyl, isobutyl, sec-butyl, t-butyl, etc.

$C_1$-$C_4$ alkoxy groups may be linear or branched. Preferable examples of such groups are methoxy, ethoxy, propoxy, isopropoxy, butoxy, isobutoxy, t-butoxy, etc.

$C_1$-$C_4$ alkylamino groups may be linear or branched. Preferable examples of such groups are methylamino, ethylamino, propylamino, isopropylamino, butylamino, isobutylamino, t-butylamino, etc.

Examples of halogen atoms are F, Cl, Br and I.

In the present invention, an especially preferable compound represented by formula (1) is nelfinavir, represented by formula (5) below.

Formula (5)

(5)

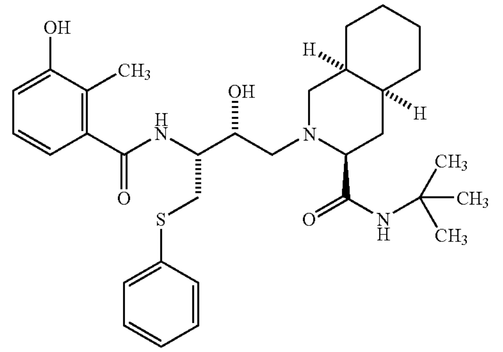

Compounds represented by formula (1) and salts thereof are capable of inhibiting the propagation of coronaviruses, and thus can treat or prevent SARS, and are particularly effective against the SARS virus. The SARS virus is not species-specific so long as the virus is a coronavirus or related species that causes SARS or a SARS-like disease.

In the present invention, the pharmaceutically acceptable salts are not limited so long as they are capable of exhibiting anti-SARS virus effectiveness. Examples are inorganic acid salts including hydrochlorides, hydrosulfates, phosphates, sulfonates, hydrobromides, etc.; and organic acid salts including acetates, oxalates, maleates, fumarates, malates, tartrates, citrates, benzoates, benzenesulfonates, p-toluene sulfonates, methanesulfonates, etc. Organic salts are preferable among these, and methanesulfonates are especially preferable.

The compounds represented by formula (1) and salts thereof can be produced by conventional methods (e.g. *Journal of Medicinal Chemistry*, Vol. 40, No. 24, pp. 3979-3985, 1997, etc.). Further, nelfinavir and methanesulfonates thereof, examples of the compound of the present invention, are known compounds which can be produced by conventional methods (e.g. *Journal of Medicinal Chemistry*, Vol. 40, No. 24, pp. 3979-3985, 1997, etc.), and even commercial products can be used.

When a compound represented by formula (1) and salt thereof is produced, it can be easily isolated and purified by typical separation methods. Examples of such methods are adsorption chromatography, preparative thin layer chromatography, recrystallization, solvent extraction, etc. Further, conventional analytical methods such as NMR and the like can confirm the production of the compound of the present invention.

Furthermore, of the compounds represented by formula (1) and salts thereof, those having free carboxy groups can form, by conventional methods, sodium salts, potassium salts and like alkali metal salts; calcium salts, magnesium salts and like alkaline earth metal salts; and other salts such as copper salts, etc. Such salts have pharmacological activities similar to those of the free compounds of the present invention, and therefore are embraced by the present invention.

Compounds represented by formula (1) and salts thereof can be used as anti-SARS agent (hereinafter referred to as "a pharmaceutical composition of the present invention") for treating SARS when used in combination with pharmaceutically acceptable carriers, excipients and/or diluents, etc., as necessary.

Usable carriers are, for example, fillers, expanders, binders, moisturizers, disintegrants, surfactants, lubricants and like diluents and excipients typically used in accordance with the preparation dosage form. Such carriers may suitably be selected for use depending on the dosage unit form of the preparation to be obtained.

The preparation can be formulated in various forms depending on the purpose of the treatment, and representative examples are tablets, pills, pulves, liquids, suspensions, capsules, suppositories, injections (liquid, suspension, etc.), sprays, aerosols, vaporoles, sustained-release microcapsules, etc.

The pharmaceutical composition of the present invention can suitably contain the active ingredient in a widely ranging proportion typically from about 0.00001 to about 70 wt. %, and preferably about 0.0001 to about 5 wt. %.

Further, in the pharmaceutical composition of the present invention, various additives such as buffers, isotonizing agents, chelating agents, etc. can be added. Examples of buffers are phosphoric acids, acetic acids, citric acids, ε-aminocaproic acids, glutamic acid and salts thereof (e.g. alkali metal salts and alkaline earth metal salts such as sodium salts, potassium salts, calcium salts, magnesium salts, etc.). Examples of isotonizing agents are sodium chloride, potassium chloride, saccharides, glycerol, etc. Examples of chelating agents are sodium edetate, citric acid, etc.

In addition to use as a liquid drug, the pharmaceutical composition of the present invention can also be freeze-dried for preservation, and, before use, dissolved in an aqueous buffer containing water, physiological saline or the like to give a suitable concentration.

Pharmaceutical compositions of the invention may further be prepared in solid dosage forms such as tablets, pills, pulves, powders, granules, capsules and the like, and in liquid dosage forms such as solutions, suspensions, emulsions, syrups, elixirs and the like. Such formulations can further be made into forms such as oral, parenteral, nasal, vaginal, suppository, sublingual tablet, ointment, are the like by following conventional methods for mixing, formulation and preparation.

Stated more specifically, for the formulation of tablets, the following drug carriers can be used as mentioned above: excipients such as lactose, white soft sugar, sodium chloride, glucose, urea, starch, calcium carbonate, kaolin, crystalline cellulose, silicic acid, calcium silicate, potassium phosphate, etc.; binders such as water, ethanol, propanol, simple syrups, glucose liquids, starch liquids, gelatin solutions, carboxymethylcellulose, hydroxypropylcellulose, methyl cellulose, polyvinyl pyrrolidone, etc.; disintegrators such as carboxymethylcellulose sodium, carboxymethyl cellulose calcium, low-substituted hydroxypropylcellulose, desiccation starch, sodium alginate, agar powder, laminaran powder, sodium hydrogencarbonate, calcium carbonate, crosspovidone, etc.; surfacants such as polyoxyethylene sorbitan fatty acid esters, sodium lauryl sulfate, stearic acid monoglycerides, etc.; disintegration inhibitors such as white soft sugar, stearin, cocoa butter, hydrogenated oils, etc.; absorption enhancers such as quaternary ammonium bases, sodium lauryl sulfate, etc.; humectants such as glycerin, starch, etc.; adsorbents such as starch, lactose, kaolin, bentonite, colloidal silicic acid, etc.; lubricants such as purified talc, stearates such as magnesium stearate, boric acid powder, polyethylene glycol, etc.; and the like.

Tablets can also be prepared as necessary in the form of coated tablets covered with conventional coatings or films, for example, sugar-coated tablets, gelatine film-coated tablets, enteric-coated tablets, film-coated tablets, and double- or multi-layered tablets.

For the formulation of pills, usable drug carriers are, for example, excipients such as glucose, lactose, starch, cacao butter, hardened vegetable oil, kaolin, talc, etc.; binders such as gum arabic powder, tragacanth powder, gelatin, ethanol, etc.; and disintegrators such as laminaran, agar, etc.

Capsules can be formed in conventional manners by mixing the above various drug carriers with the active ingredient of the present invention, and then filling the mixture into hard or soft gelatin or the like.

Liquid dosage forms for oral administration may contain routinely used inert diluents, for example, water-containing pharmaceutically acceptable solutions, emulsions, suspensions, syrups, elixirs, etc., and can further contain auxiliaries such as wetting agents, emulsions, suspension agents, etc. These can be prepared by conventional procedures.

Liquid dosage forms for parenteral administration, such as sterilized aqueous-or non aqueous-solutions, emulsions, suspensions, etc., can be formulated by using diluents, e.g. water, ethyl alcohol, propylene glycol, polyethylene glycol, ethoxylated isostearyl alcohol, polyoxylated isostearyl alcohol, polyoxyethylene sorbitan fatty acid esters and vegetable oils such as olive oil, etc. Injectable organic esters, such as ethyl oleate, can also be admixed. Furthermore, routinely used solubilizing agents, buffers, wetting agents, emulsifiers, suspension agents, preservatives, dispersants, etc. can be added. Sterilization can be carried out by, for example, a filtration operation in which the preparation is passed through a bacterial filter; mixed with a sterilant; irradiated; heat treated and/or the like. The preparation can also be formulated in the form of a sterilizable solid composition such that it can be dissolved in sterile water or like medium suitable for sterilizing immediately before use.

For the formulation of suppository and vaginal dosage forms, usable drug carriers are, for example, polyethylene glycol, cacao butter, higher alcohols, esters of higher alcohols, gelatin, semisynthetic glyceride, etc.

Compositions for spray, aerosol, vaporole, nasal and sublingual dosages can be prepared using known standard excipients by following conventional methods.

Pharmaceutical compositions of the present invention may further contain, as appropriate, coloring agents, preservatives, perfumes, flavors, sweeteners, other drugs and the like.

The administration routes of the above pharmaceutical preparations are not limited, and can be accordingly determined based on the preparation form; age, sex, other conditions of patient; severeness of symptoms, etc. For example, tablets, pills, liquids, suspensions, emulsions, granules and capsules are orally administered, and injectable forms are intravenously administered singularly or in combination with typical replacement fluids such as those containing glucose, amino acids, etc., or if necessary, can be administered as they are intramuscularly, endermically, subcutaneously or intra-abdominally. Suppositories are rectally administered, vaginal forms are vaginally administered, nasal forms are intranasally administered and sublingual forms are intraorally administered.

Dosages of the above pharmaceutical preparations are not limited, and can be selected from wide ranges based accordingly to the desired treatment efficacy, administration route, treatment period, age, sex and other conditions of the patient, etc. The preparation is typically administered in a dose of about 0.01 mg to about 100 mg, and preferably about 0.1 mg to about 50 mg, per 1 kg of body weight per day per adult in terms of the active ingredient, in one to several portions a day.

Further, in the treatment method of the present invention, the anti-SARS agent can concurrently be used with, for example, other antiviral agent.

BEST MODE FOR CARRYING OUT THE INVENTION

Preferred embodiments of the present invention are described in more detail below with reference to examples. However, the invention is not limited to these examples.

EXAMPLE 1

Vero cells obtained from Dr. Doerr of the Frankfurt University were placed in a 96-well plate, and incubated for 1 day to achieve confluency. The culture medium was then replaced, and commercial nelfinavir methanesulfonate in various concentrations (40 nM, 200 nM, 1 μM, 5 μM, 10 μM, 50 μM) or commercial glycyrrhizin in various concentrations (1 μM, 10 μM, 100 μM) was added.

One hour after the addition of nelfinavir or glycyrrhizin, the Vero cells were infected with the SARS virus. Thirty-six hours after the cells were infected with the SARS virus, the efficacy of the compound of the present invention was evaluated based on the Vero cell viability using an MTT assay, and the $EC_{50}$ (the concentration of compound required to inhibit cytopathic effects by viral infection to 50% of the control value), $CC_{50}$ (the cytotoxic concentration of compound required to destroy 50% of verotoxin cells) and SI (=$CC_{50}$/$EC_{50}$) were calculated. Table 1 shows the results.

TABLE 1

| Compound | $EC_{50}$ (μM) | $CC_{50}$ (μM) | SI (Selection Index) |
|---|---|---|---|
| Nelfinavir | 0.0484 | 14.6 | 301.6 |
| Glycyrrhizin | 364.5 | >24304 | >66 |

This table demonstrates that nelfinavir is extremely more anti-SARS virus potent than glycyrrhizin, a positive control. Moreover, the cytotoxicity of nelfinavir was found to be extremely low compared with that of glycyrrhizin.

Furthermore, morphology and destruction kinetics of Vero cells at a nelfinavir concentration of 10 μM were observed using an optical microscope, and electron micrographs (FIG. 1A and FIG. 1B) were also taken. FIG. 1A shows that the Vero cells to which nelfinavir was not added were found to have been destroyed by the proliferation of the SARS virus. FIG. 1B shows that the nelfinavir-added Vero cells had the same morphology as normal cells because the proliferation of SARS virus was inhibited.

Under the same experimental conditions, Vero cells were further observed by an immunofluorescence antibody method. FIG. 1C shows that the SARS virus infection had remarkably spread in the cells to which nelfinavir was not added.

FIG. 1D also shows that the SARS virus infection was advantageously controlled in the nelfinavir-added Vero cells.

Under the same experimental conditions, RNA levels of the SARS virus in Vero cells were quantified using RT-PCR. The results are shown in FIG. 1E, which demonstrates that nelfinavir is highly inhibitive against the propagation of the SARS virus.

COMPARATIVE EXAMPLE 1

Experiments were performed in the same manner as in Example 1, except that in place of nelfinavir the following compounds represented by formulas (7) to (12) were used.

Formula (7):
(7)
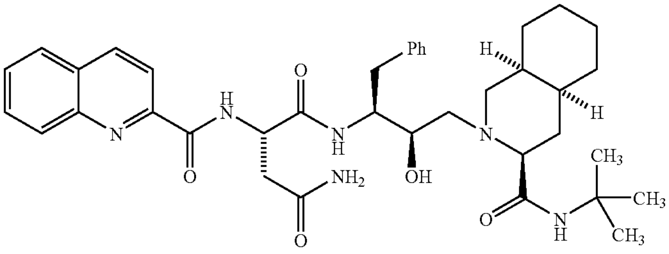
saquinavir
Formula (8):
(8)
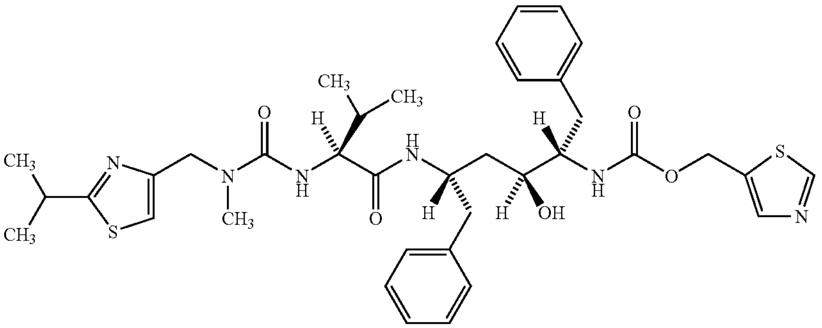
ritonavir
Formula (9):
(9)
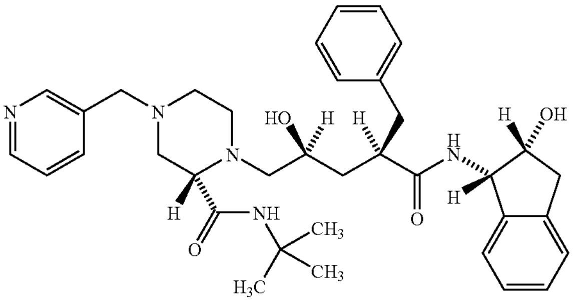
crixivan
Formula (10):
(10)
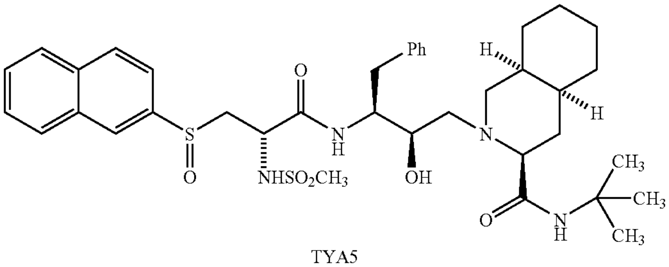
TYA5

-continued

Formula (11):

(11)

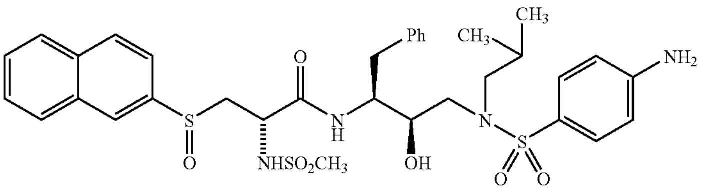

TYB5

Formula (12):

(12)

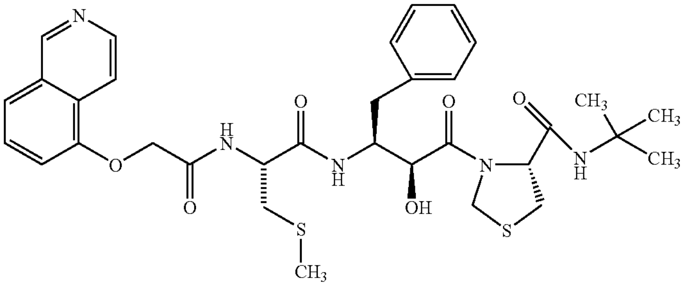

KNI-272

None of the above compounds exhibited anti-SARS virus efficacies at a compound concentration of 10 μM (data not shown).

INDUSTRIAL APPLICABILITY

The present invention provides an anti-coronavirus agent comprising as an active ingredient a compound represented by formula (1) or salt thereof, an anti-SARS agent comprising the anti-coronavirus agent and a method of treating SARS using the anti-SARS agent. The present invention enables the treatment of diseases caused by coronaviruses, especially the SARS-associated coronavirus.

The invention claimed is:

1. A method for treating SARS in a patient in need of treatment using an anti-SARS-associated coronavirus agent comprising as the active ingredient a compound represented by formula (5).

Formula (5)

(5)

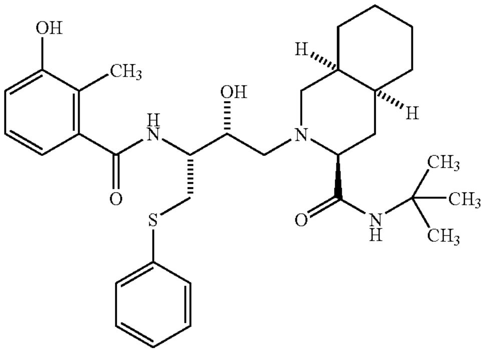

or a pharmaceutically acceptable salt thereof.

2. A method for treating SARS according to claim 1, wherein the pharmaceutically acceptable salt of the compound represented by formula (5) is a methanesulfonate.

3. A method for treating SARS using an anti-SARS-agent comprising the anti-SARS-associated coronovirus agent according to claim 1 as an active ingredient, and a pharmaceutically acceptable carrier, excipient and/or diluent.

* * * * *